United States Patent
Lowe et al.

(10) Patent No.: US 9,814,747 B2
(45) Date of Patent: Nov. 14, 2017

(54) **METHODS FOR INHIBITING HIV-1 ACTIVITY BY INHIBITORY MECHANISMS OF EXTRACTS OF *GUAIACUM OFFICINALE* L. (ZYGOPHYLLACEAE)**

(71) Applicants: Henry Lowe, West Indies (JM); Ngeh J. Toyang, Columbia, MD (US); Joseph Bryant, Baltimore, MD (US)

(72) Inventors: Henry Lowe, West Indies (JM); Ngeh J. Toyang, Columbia, MD (US); Joseph Bryant, Baltimore, MD (US)

(*) Notice: Subject to any disclaimer, the term of this patent is extended or adjusted under 35 U.S.C. 154(b) by 0 days.

(21) Appl. No.: 14/805,324

(22) Filed: Jul. 21, 2015

(65) Prior Publication Data
US 2017/0020940 A1 Jan. 26, 2017

Related U.S. Application Data

(60) Provisional application No. 62/026,844, filed on Jul. 21, 2014.

(51) Int. Cl.
*A01N 65/00* (2009.01)
*A61K 36/185* (2006.01)
*A61K 31/704* (2006.01)

(52) U.S. Cl.
CPC .......... *A61K 36/185* (2013.01); *A61K 31/704* (2013.01)

(58) Field of Classification Search
CPC ..................................................... A61K 36/00
USPC ....................................................... 424/725
See application file for complete search history.

(56) References Cited

FOREIGN PATENT DOCUMENTS

KR 20100027360 A * 3/2010

OTHER PUBLICATIONS

Cragg G, Newman D. Plants as a source of anti-cancer and anti-HIV agents, Annals of Applied Biology, 143:127-33 (2003).
Yang SS, Cragg GM, Newman DJ, Bader JP, Natural product-based Anti-HIV Drug Discovery and Development Facilitated by the NCI Developmental Therapeutics Program, Journal of Natural Products, 64:265-77 (2001).
Boyd MR, Hallock YF, Cardellina JH et al., Anti-HIV Michellamines From Ancistrocladus Korupensis. Journal of Medicinal Chemistry, 37:1740-5 (1994).
Fujioka T, Kashiwada Y, Kilkuskie RE, et al., Anti-AIDS Agents, Betulinic Acid and Platanic Acid As Anti-HIV Principles From Syzigium Claviflorum and the Anti-HIV Activity of Structurally Related Triterpenoids, Journal of Natural Products, 57:243-7 (1994).
Singer G., Lignum Vitae, Guaiacum officinale at http://wwwstjohnbeachguidecom/Lignum%20Vitaehtm.
Halberstein R., Traditional Botanical Remedies on a Small Caribbean Island: Middle (Grand) Caicos, West Indies. The Journal of Alternative and Complementary Medicine, 3:227-39.,7 (1997).
Halberstein RA., Medicinal Plants: Historical and Cross-Cultural Usage Patterns, Annals of Epidemiology, 15:686-99 (2005).
Ahmad VU, Perveen S, Bano S., Saponins from the Leaves of Guaiacum officinale, Phytochemistry, 29:3287-90 (1990).
Ahmad VU, Saba N, Khan KM., Triterpenoid Saponin From the Bark of *Guaiacum officinale* L., Natural Product Research, 18:111-6 (2004).
Ahmad VU, Perveen S, Bano S., Guaiacin A and B from the Leaves of Guaiacum officinale, Planta Medica, 55:307-8 (1989).
Saba N. Guaianin N, A New Saponin From Flowers of Guaiacum Officinale, Pakistan Journal of Scientific and Industrial Research, 36:54-56 (1993).

* cited by examiner

Primary Examiner — Michael Meller
(74) Attorney, Agent, or Firm — Baker Donelson, PC; Royal W. Craig (57) ABSTRACT

A therapeutic phenolic extract derived from plant biomass, and more specifically the indigenous Jamaican plant *guaiacum officinale* L. (Zygophyllaceae), for use in regressing or controlling HIV-1 replication in infected patients, and to help prevent sexual transmission of HIV-1, as well as the method for inhibiting HIV-1 by administering a pharmaceutically-acceptable amount of the crude extract to prevent HIV-viral replication without causing excessive damage to normal cells.

9 Claims, 3 Drawing Sheets

Table 2. SUMMARY OF ANTIPROLIFERATIVE ACTIVITY OF GUAIACUM (JOM) COMPOUNDS AND ANALOGS USING WST-1 ASSAY (IC$_{50}$=μg/ml)

| Sample ID | RTI Ref # | A375 | PC-3 | DU-145 | MCF-7 | MDA-MB231 | A549 | HCT-116 | HL-60 |
|---|---|---|---|---|---|---|---|---|---|
| JOMCP-001 | N/A | 15.52±0.59 | 17.02±5.17 | | 25.6±0.82 | | | | |
| JOMCP-001-F1 | JOMCP001-F1 | NT | NT | NT | NT | NT | NT | NT | NT |
| JOMCP-001-F2A | JOMCP001-F2A | NT | NT | NT | NT | NT | NT | NT | NT |
| JOMCP-001-F2B | JOMCP001-F2B | NT | NT | NT | NT | NT | NT | NT | NT |
| HL-016 | 13227-42B | >100 | >100 | >100 | >100 | >100 | >100 | >100 | >100 |
| HL-017 | 13227-45 | 36.12 | 8.3 | 9.6 | >100 | NT | 10.3 | NT | 6±1.97 |
| HL-018 | 13227-49A | 22.4 | 12.5 | 11.6 | 18.1 | NT | >100 | NT | 13.5 |
| HL-019 | 13227-52A | >100 | >100 | >100 | >100 | NT | NT | NT | >100 |
| HL-020 | 13227-56B | >50 | 12.6 | >100 | >100 | NT | NT | >100 | >100 |
| HL-021 | 13227-55 | >100 | >100 | >100 | >100 | NT | NT | >100 | >100 |
| HL-028 | 13227-000 | >100 | >100 | >100 | >100 | NT | NT | >100 | >100 |
| HL-029 | 13227-39 | >100 | >100 | >100 | >100 | NT | NT | >100 | >100 |
| HL-030 | 13227-86A | >100 | >100 | >100 | >100 | NT | NT | >100 | >100 |
| HL-031 | 13227-87 | >100 | >100 | >50 | >100 | >50 | NT | >100 | >100 |
| HL-032 | 13227-89B | >100 | >100 | >100 | >100 | NT | NT | >100 | >100 |
| HL-034 | 13227-095A | >100 | >100 | >100 | >100 | NT | NT | >100 | >100 |
| HL-035 | 13227-123B | >100 | >100 | >100 | >100 | NT | NT | >100 | >100 |
| HL-036 | 13227-127 | >100 | >100 | >100 | >100 | NT | NT | >100 | >100 |
| HL-037 | 13227-129A | >100 | >100 | >100 | >100 | NT | NT | >100 | >100 |
| HL-038 | 13227-179A/34A | 11.1±3.81 | 15.05±4.17 | >100 | >100 | NT | NT | 10.75±1.76 | NT |
| HL-039 | 13227-132B | >100 | >100 | >100 | >100 | NT | NT | >100 | >100 |
| HL-040 | 13227-198B | >100 | >100 | >100 | >100 | NT | NT | >100 | >100 |
| HL-041 | 13596-005AD | >100 | >100 | >100 | >100 | NT | NT | >100 | >100 |
| HL-042 | 13596-009A | >100 | >100 | | >100 | NT | NT | | |

NT=Not tested

FIG. 3

Table 2

| Sample ID | RTI Reference # | MTT (IC$_{50}$ µg/ml)- Cytotoxicity[a] | P$^{24}$ (EC$_{50}$ µg/ml)- HIV[b] | Selectivity index (a/b) |
|---|---|---|---|---|
| JOMCP001 | N/A | 10 | 4 | 2.5 |
| JOMCP001-F1 | JOMCP001-F1 | >100 | 14.41 | 6.9 |
| JOMCP001-F2A | JOMCP001-F2A | 6.039 | 2.717 | 2.22 |
| JOMCP001-F2B | JOMCP001-F2B | 6.873 | 2.827 | 2.43 |
| HL-016 | 13227-42B | Toxic | NA | NA |
| HL-017 | 13227-45 | 9.759 | 5.405 | 1.805 |
| HL-018 | 13227-49A | 8.751 | 1.83 | 4.781 |
| HL-019 | 13227-52A | Toxic | NA | NA |
| HL-020 | 13227-56B | 9.3 | 0.8 | 11.62 |
| HL-021 | 13227-55 | Toxic | NA | NA |
| HL-028 | 13227-000 | Toxic | NA | NA |
| HI-029 | 13227-39 | Toxic | NA | NA |
| HI-030 | 13227-86A | >100 | >100 | NA |
| HL-031 | 13227-87 | >100 | >100 | NA |
| HL-032 | 13227-89B | >100 | >100 | NA |
| HL-034 | 13227-095A | OR | OR | - |
| HL-035 | 13227-123B | 1.1 | 17 | .064 |
| HL-036 | 13227-127 | 0.5 | 0.4 | 1.25 |
| HL-037 | 13227-129A | 0.5 | 0.4 | 1.25 |
| HL-038 | 13227-179A/34A | 4.59 | 1.8 | 2.55 |
| HL-039 | 13227-132B | toxic | NA | NA |
| HL-040 | 13227-198B | Toxic | NA | NA |
| HL-041 | 13596-005AD | Toxic | NA | NA |
| HL-042 | 13596-009A | 18.79 | 423.4 | 0.044 |
| | | | | |

FIG. 4

METHODS FOR INHIBITING HIV-1 ACTIVITY BY INHIBITORY MECHANISMS OF EXTRACTS OF *GUAIACUM OFFICINALE* L. (ZYGOPHYLLACEAE)

CROSS-REFERENCE TO RELATED APPLICATION(S)

The present application derives priority from U.S. Provisional Patent Application 62/026,844, filed 21 Jul. 2014, the entirety of which is incorporated herein by reference.

BACKGROUND OF THE INVENTION

1. Field of the Invention

The present invention relates to drugs for inhibiting lentiviral activity and, more particularly, to a method for suppressing replication of the human immunodeficiency virus (HIV) by inhibitory mechanisms of a class of a crude extract of *guaiacum officinale* L. (Zygophyllaceae).

2. Description of the Background

There is great growth in the overlapping fields of biology, technology, and medicine, including remarkable advances in cellular biology that have given a new understanding of the molecular basis for some diseases. Nevertheless, there is currently no cure for HIV/AIDS. A number of natural products, mainly from plants, have been shown to possess anti HIV activity [Cragg G, Newman D. Plants as a source of anti-cancer and anti-HIV agents, Annals of Applied Biology, 143:127-33 (2003)]. This has resulted in the screening of thousands of plant extracts in search of effective drugs against HIV [Yang S S, Cragg G M, Newman D J, Bader J P, Natural product-based Anti-HIV Drug Discovery and Development Facilitated by the NCI Developmental Therapeutics Program, Journal of Natural Products, 64:265-77 (2001)]. The michellamine series of alkaloids and derivatives of betulinic acid are amongst some of the molecules isolated from plants with anti HIV activity [Boyd M R, Hallock Y F, Cardellina J H et al., Anti-HIV Michellamines From Ancistrocladus Korupensis. Journal of Medicinal Chemistry, 37:1740-5 (1994); Fujioka T, Kashiwada Y, Kilkuskie R E, et al., Anti-AIDS Agents, Betulinic Acid And Platanic Acid As Anti-HIV Principles From Syzigium Claviflorum And The Anti-HIV Activity Of Structurally Related Triterpenoids, Journal of Natural Products, 57:243-7 (1994)].

The Jamaican national flower, *guaiacum officinale* L., belongs to the Zygophyllaceae family and is commonly known as Lignum vitae. The plant is known to have a number of medicinal uses in folk medicine. For example, mixtures containing barks from *guaiacum officinale* L. and Maubi have been used in traditional Virgin Islands bush medicine to relieve fish poisoning [Singer G., Lignum Vitae, *Guaiacum officinale* at http://wwwstjohnbeachguidecom/Lignum%20Vitaehtml]. The flowers and leaves have been used to make a tea with energy restorative properties and as abortificient [Halberstein R., Traditional Botanical Remedies on a Small Caribbean Island: Middle (Grand) Caicos, West Indies. The Journal of Alternative And Complementary Medicine, 3:227-39, 7 (1997), Halberstein R A., Medicinal Plants: Historical And Cross-Cultural Usage Patterns, Annals of Epidemiology, 15:686-99 (2005)].

Elsewhere, there is anecdotal evidence that certain resins and extracts of *guaiacum officinale* L. have anti-inflammatory properties with activity against arthritis, gout and sciatica condition, and the resins of the plant are used in traditional medicines in Pakistan to cure angina, tonsillitis, rheumatoid arthritis, mucous membrane diseases and abnormalities of metabolic processes.

*Guaiacum Officinale* L. is known to be a rich source of saponins. Saponins are credited for several biological activities including membrane-permeabilising, immunostimulation and hypocholesterolaemic properties. Several mono and bidesmosidic saponins having akebonic acid and oleanolic acid as genins have previously been isolated and reported from this plant [Ahmad V U, Perveen S, Bano S., Saponins from the Leaves of *Guaiacum officinale*, Phytochemistry, 29:3287-90 (1990); Ahmad V U, Saba N, Khan K M., Triterpenoid Saponin From The Bark Of *Guaiacum Officinale* L., Natural Product Research, 18:111-6 (2004)]. Two *guaiacum* saponins, Guaiacin A and B, have been isolated from the leaves of *Guaiacum officinale* L. [Ahmad V U, Perveen S, Bano S., Guaiacin A and B from the Leaves of *Guaiacum officinale*, Planta Medica, 55:307-8 (1989)]. More recently, a new triterpenoidal saponin, guaianin N was isolated from the butanolic extract of the flowers of *Guaiacum officinale* L. [Saba N. Guaianin N, A New Saponin From Flowers Of *Guaiacum Officinale*, Pakistan Journal of Scientific and Industrial Research, 36:54-56 (1993)]. The Guaianin N showed antibacterial activity against *Pseudomonas* pseudomaliae as well as brine shrimp toxicity.

The present inventors have extracted a class of disaccharide arabinogalactan isolates from the indigenous plant and have applied them therapeutically to selectively inhibit HIV-1 in primary peripheral blood mononuclear cells (PBMCs) infected with the reference HIV-1 BaL strain, without substantial cytotoxicity activity to the PBMCs. Arabinogalactan is a biopolymer consisting of arabinose and galactose monosaccharides. The extract holds promise as a chemopreventive agent.

SUMMARY OF THE INVENTION

It is, therefore, the primary object of the present invention to provide a method for inhibiting HIV-1 by administering a pharmaceutically-acceptable amount of a crude extract of the indigenous Jamaican plant *guaiacum officinale* L. (Zygophyllaceae) containing one or more disaccharide arabinogalactan isolates to help control HIV-1 replication in infected patients, and to help prevent s sexual transmission of HIV-1.

BRIEF DESCRIPTION OF THE DRAWINGS

Other objects, features, and advantages of the present invention will become more apparent from the following detailed description of the preferred embodiments and certain modifications thereof when taken together with the accompanying drawings in which:

FIG. 3 is a table of the bioassay results for anti HIV activity.

DETAILED DESCRIPTION OF THE PREFERRED EMBODIMENTS

The present invention is a therapeutic phenolic extract derived from plant biomass, and more specifically the indigenous Jamaican plant *guaiacum officinale* L. (Zygophyllaceae), for use in regressing or controlling HIV-1 replication in infected patients, and to help prevent sexual transmission of HIV-1, as well as the method for inhibiting HIV-1 by administering a pharmaceutically-acceptable amount of the crude extract to prevent HIV-viral replication without causing excessive damage to normal cells.

Preparation of the *Guaiacum Officinale* L. Extracts

The whole *Guaiacum Officinale* L. plant was collected by hand from plants in Kingston, Jamaica. A voucher specimen of the plant was identified at the University of the West Indies, Mona Herbarium, and was deposited under Accession Numbers: 35724 and 35725. The collected plant material was air dried away from direct sunlight and pulverized. The leaves, seeds and twigs of ground *G. officinale* L. were extracted with methanol at room temperature for 48 hrs. The filtered solutions were dried in a rotary evaporator. Table 1 presents the details of the extraction process.

TABLE 1

Extraction of different parts of *G. officinale* L.

| Plant Part | Solvent  | Volume | Amount (kg) | Yield (g) | % Yield |
|------------|----------|--------|-------------|-----------|---------|
| Leaf       | Methanol | 6 L    | 1.20        | 58.4      | 4.87    |
| Seeds      | Methanol | 2 L    | 0.35        | 25.31     | 7.23    |
| Twigs      | Methanol | 3 L    | 0.50        | 18.20     | 3.64    |

To obtain the ethyl acetate fraction, 1.0 g of the crude methanolic extract was extracted with ethyl acetate 3×20 mL. The extract was concentrated in a speedvac yielding 0.214 g of the ethyl acetate soluble portion. A sample of each extract was dissolved in DMSO and stored at −20° C. The samples were subsequently diluted as necessary prior to use in an anti-HIV assay.

Bio-Assay of Crude Extracts

Stocks of crude drug made from *G. officinale* L. were prepared in Dimethyl sulfoxide (DMSO) in a stock solution of 10 mg/ml. Dilutions from the stock were made and the final concentration of DMSO in the cultures was always <0.1% to avoid cell toxicity. Peripheral blood mononuclear cells (PBMCs) were separated from buffy coats of HIV-1 seronegative donors (New York Blood Center, NY) by density centrifugation over Ficoll-Hypaque (Sigma). Briefly, the buffy coat suspension was diluted 1:2 with phosphate-buffered saline solution (PBS). Then, 35 ml were layered onto 15 ml of Ficoll® Paque PLUS (GE Healthcare), a ready to use sterile medium for isolation of lymphocytes and were centrifuged by standard ficoll-paque gradient centrifugation according to manufacturer's protocol (GE Healthcare) for 25 min at 400×g. The white interphase containing the PBMCs was collected and washed three times with PBS. PBMCs were cultured in 5% CO2 at 37° C., in RPMI-1640 medium (available from Sigma-Aldrich) supplemented with L-glutamine (300 mg/ml), penicillin/streptomycin (10 U/ml) and 10% heat inactivated fetal bovine serum (FBS). For infection of PBMCs, the CCR5 tropic HIV-1 reference strain HIV-1 BaL was used. Prior to infection, PBMCs were first activated by culture in RPMI-10 medium containing 2.5 µg/ml of the mitogen phytohemagglutinin (PHA; Roche, Indianapolis, Ind.) for 3 days. PHA activation renders PBMCs highly susceptible to productive infection with HIV-1. Following 3 days, PBMCs were infected by incubation with virus at a multiplicity of infection (MOI) of 0.001 for 2 hours. PBMCs were then washed three times with PBS to remove residual virus and seeded in 96-well flat-bottom plates at a density of 2×105 PBLs/200 µL in RPMI-10 supplemented with 10 units/ml of the growth factor Interleukin 2 (IL-2; Roche) and drugs. IL-2 addition is required for optimal proliferation of cultured PBMCs. Following 3 days of culture, half of the medium was discarded and replenished with fresh medium containing IL-2 and drugs at the same final concentration as before. This step helps maintain viability of cultured cells and drug activity. On day 7, HIV-1 p24 protein production in the culture supernatant was measured using a commercial ELISA kit (Coulter, Hialeah, Fla.) and cell viability using a colorimetric MTT kit (Roche). The MTT test is based on the reduction of the yellow colored MTT (3-(4,5-dimethylthiazol-2-yl)-2,5-diphenyltetrazolium bromide) to blue formazan by mitochondrial dehydrogenases. The quantity of formazan produced (absorbance at 490 nm) is directly proportional to the number of living cells. Briefly, cell aliquots were seeded in 96-well plates (100 µl) and incubated with 10 µl of MTT solution for 4 h at 37° C. A solubilization solution (50 µl) was added and plates incubated overnight at 37° C. MTT conversion to formazan by mitochondrial dehydrogenase was assayed by optical density at 490 nm measured in an ELISA plate reader. MTT assays were also European Journal of Medicinal Plants, 4(4): 483-489, 2014 486 conducted on uninfected PHA-activated PBMCs cultured in the presence of serial dilutions of each drug to assess toxicity.

Select Class of Phytochemicals

The inventors undertook to identify the phytochemicals responsible for the observed anti-HIV activities in *Guaiacum Officinale* L. and to further isolate and synthesize these phytochemicals. Identification of the various components was based on liquid chromatography/mass spectroscopy (LC/MS) ions as correlated to literature data. From a sample of the isolate, nuclear magnetic resonance spectra were obtained on a Varian Inova 500 MHz NMR spectrometer. Proton spectra were obtained over a sweep width 6500 Hz (13 ppm) and the carbon spectra were obtained over a sweep width of 25000 Hz (200 ppm). Two dimensional proton-proton correlation spectra (gCOSY), rotational frame over-hauser enhanced spectroscopy (ROESY), and Total correlation spectroscopy (TOCSY) were obtained over a sweep width of 3100 Hz with a 1 sec interpulse delay. The gCOSY spectrum was obtained in 16 repetitions per increment as a 1K×128 point data matrix then zero filled and fourier transformed to a 2K×2K data point two dimensional spectrum. The ROESY and TOCSY spectra were obtained in 128 repetitions as a 1K×400 point data matrix then fourier transformed to a 2K×2K two dimensional spectra. A mixing time of 400 mS was used for the ROESY spectrum and 80 mS mixing time for the TOCSY spectrum. Two dimensional proton—carbon heteronuclear single quantum correlation spectra (gHSQC) and heteronuclear multiple bond correlation spectra (gHMBC) were each obtained over a sweep width of 3100 Hz×25000 Hz as a 1K×512 point data matrix in 128 repetitions per increment. Both spectra were zero filled and fourier transformed to a 2K×2K data point two dimensional spectrum. A 135 Hz coupling constant was used for gHSQC detection and an 8 Hz coupling constant was used for gHMBC detection. The Carbon and proton NMR data is presented on Table 1.

| Carbon Chemical Shift | Multiplicity | Proton Chemical Shift |
|-----------------------|--------------|-----------------------|
| 15.13                 | CH3          | 0.86                  |
| 16.14                 | CH           | 0.73                  |
| 16.43                 | CH3          | 0.74                  |
| 16.83                 | CH3          | 0.7                   |
| 17.79                 | CH2          | 1.03, 1.45            |
| 22.60                 | CH2          | 1.46, 1.89            |
| 22.91                 | CH2          | 1.78                  |

-continued

| Carbon Chemical Shift | Multiplicity | Proton Chemical Shift |
|---|---|---|
| 23.38 | CH3 | 0.86 |
| 25.54 | CH3 | 1.08 |
| 25.71 | CH2 | 1.54, 1.70 |
| 27.19 | CH2 | 1.00, 1.63 |
| 27.49 | CH3 | 0.96 |
| 27.60 | CH3 | 0.96 |
| 30.40 | C | — |
| 32.07 | CH2 | 0.86, 1.59 |
| 32.37 | CH2 | 1.22, 1.42 |
| 32.83 | CH | 0.86 |
| 33.30 | CH2 | 1.12, 1.30 |
| 36.32 | C | — |
| 38.03 | CH2 | 0.91, 1.50 |
| 38.69 | C | — |
| 38.80 | C | — |
| 38.87 | C | — |
| 40.80 | CH | 2.73 |
| 41.32 | C | — |
| 45.45 | C | — |
| 45.67 | CH2 | 1.05, 1.59 |
| 47.01 | CH | 1.49 |
| 54.96 | CH | 0.71 |
| 60.81 | CH2 | 3.45, 3.59 |
| 60.98 | CH2 | 3.40, 3.62 |
| 63.07 | CH2 | 3.31, 3.65 |
| 63.33 | C | 3.32, 3.64 |
| 65.77 | CH2 | 3.39, 3.63 |
| 66.32 | CH | 3.64 |
| 67.36 | CH | 3.8 |
| 69.81 | CH | 3.07 |
| 69.85 | CH | 3.05 |
| 69.96 | CH | 3.47 |
| 71.21 | CH | 3.57 |
| 72.55 | C | — |
| 73.86 | CH | 3.03 |
| 74.51 | CH | 2.95 |
| 76.25 | CH | 3.12 |
| 76.36 | CH | 3.12 |
| 76.75 | CH | 3.06 |
| 76.81 | CH | 3.06 |
| 78.55 | CH | 3.64 |
| 82.93 | CH | 3.42 |
| 87.84 | CH | 3.01 |
| 87.90 | CH | 3.01 |
| 103.31 | CH | 4.32 |
| 103.79 | CH | 4.31 |
| 104.34 | CH | 4.35 |
| 105.68 | CH | 4.16 |
| 121.51 | CH | 5.14 |
| 143.81 | C | — |
| 178.59 | C | — |

For molecular weight analysis, a 1.5 mg portion of JOMCP-001 was dissolved in 1 ml of 50:50 mixture of methanol and water. The solution was further diluted to approximately 5 ug/ml for mass spectrometric analysis performed on a Waters Synapt G2 High Definition Ion Mobility mass spectrometer. Data were obtained in Exact Mass mode, MS/MS mode and ion drift mode.

Three pieces of valuable information were obtained from the mass spectrometry data. Examination of the ion under exact mass conditions yields an m/z of 749.4483 (100% intensity, M) 750.4518 (45% intensity, M+1), 751.4539 (10% intensity, M+2) in the negative ion mode. This calculated the most probable neutral molecular formula as $C_{41}H_{66}O_{12}$.

Analysis of the daughter ions of the parent ion show two main fragment ions as depicted below:

The largest fragment m/z=587.3984 (100% intensity, M), 588.4044 (40% intensity, M+1), 589.4112 (8% intensity, M+2) and a smaller fragment m/z=455.3561 (20% intensity, M), 456.3631 (8% intensity, M+1). These fragments are consistent with a loss of $C_6H_{10}O_5$ to produce the m/z=588.4044 fragment and a further loss of $C_5H_8O_4$ to produce the m/z=455.3561 fragment.

Mass spectrometry and NMR analysis identified the sample of JOMCP-001 as a mixture of two isomers. Both isomers have an Oleanolic acid core. Both isomers have a $C_{11}O_9$ disaccharide attached to the Oleanolic acid core at the hydroxyl. One of the isomers is a pentose attached to the core with a hexose attached to the pentose. The other isomer is some other, yet similar, arrangement.

Figure 1:
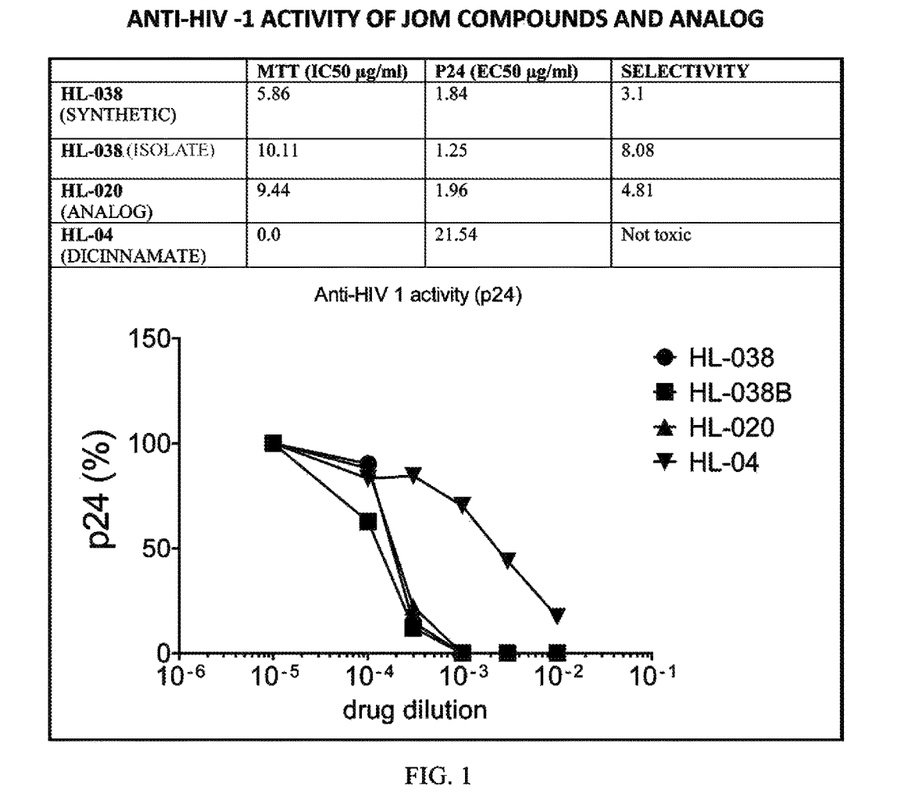
FIG. 1 illustrates the Anti-HIV-1 activity of isolates and synthetics in accordance with the invention.
Figure 2:
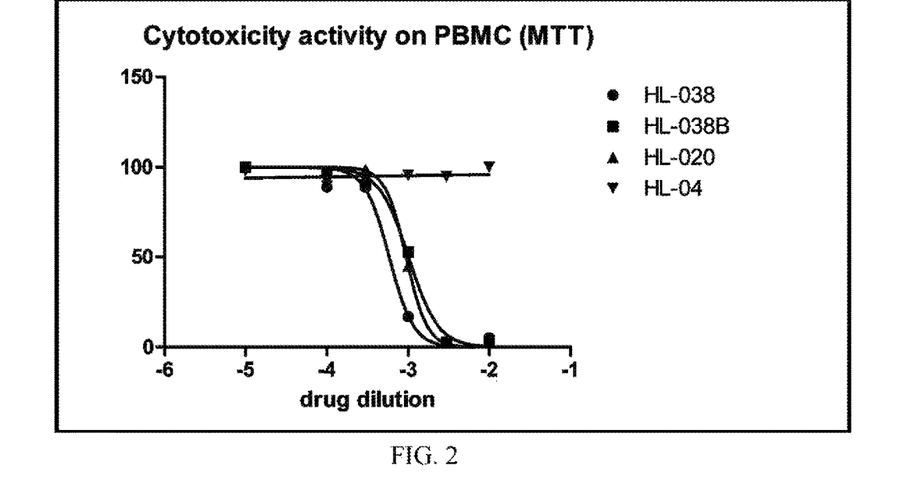
FIG. 2 illustrates the Anti-HIV-1 activity of isolates and synthetics in accordance with the invention.

The combination of the isomers fulfilled all of the requirements of the spectral data obtained with the structures, as presented in FIG. 1.

To obtain analogs of the isomers for biological activity screening, several components including HL-020 and HL-038 were synthesized based on the following general scheme:

-continued

Several analogs were synthesized belonging to the following glycoside groups:
- Galactose Analogs
- Lactose Analogs
- α-D-Arabinopyranose Analogs
- 2-Deoxyglucose Analogs
- Galactose-Arabinopyranose Analogs Specifically, the HL-038 is a Galactose-Arabinopyranose Analog having the following chemical formula:

HL-038

The HL-020 is a Lactose Analog having the following chemical formula:

HL-020

Each isolate may be synthesized by known methods. See, Koji Nakanishi, Natural Products Chemistry, University Science Books (1983).

Test Results

Figure 4:
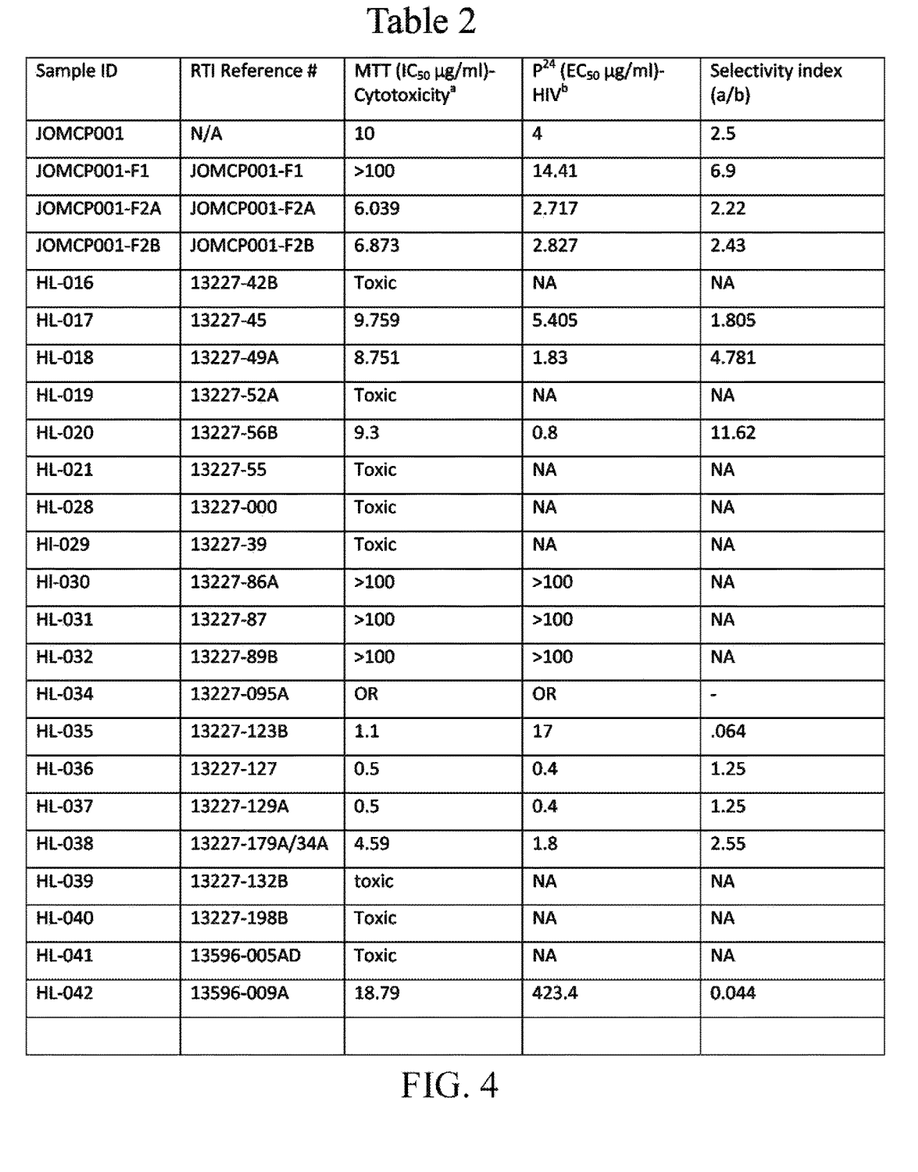
FIG. 4 is a table of the cell proliferation assay.

The anti-HIV activity of the foregoing isolates and synthetics was assessed by bioassay. The isolate and two of their synthetics proved effective, and their Anti-HIV-1 activity is shown in FIG. 1. Three additional compounds (JOMCP001-F1, JOMCP001-F2A and JOMCP001-F2B) were subsequently separated and bioassayed. The bioassay complete results for anti HIV activity and cell proliferation assays are indicated in FIG. 3 and FIG. 4, respectively, in which dicinnamate (HL-04) is included for reference as a compound isolated from a different plant and arising through synthesis (FIG. 1). JOMCP001-F1, JOMCP001-FA2 and JOMCP001-F2B are also compounds isolated from *Guaiacum officinalis* L. (a.k.a. "JOM") and are close structural analogs of the compounds depicted above. JOMCP001-F2A and JOMCP001-F2B are considered active compounds.

The results indicate that the natural isolate (JOMCP-001) as well as its close analog HL-038 exhibited moderate activity against 3 cancer cell lines (FIG. 3) and against the HIV-1 virus (FIG. 3). The compounds including other analogs synthesized are therapeutically effective in regressing or controlling HIV-1 replication and may help prevent sexual transmission of HIV-1, by preventing HIV-viral replication without causing excessive damage to normal cells.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

We claim:

1. A method for inhibiting HIV-1 in a human or animal in need thereof comprising:
   obtaining a quantity of indigenous Jamaican plant *Guaiacum Officinate* L.;
   extracting a disaccharide arabinogalactan from said indigenous Jamaican plant *Guaiacum Officinale* L.;
   administering a therapeutically effective amount of said disaccharide arabinogalactan into the bloodstream of said human or animal in need thereof to expose the primary peripheral blood mononuclear cells of the patient thereto;
   said therapeutically effective amount of said disaccharide arabinogalactan eliciting an inhibitory response of HIV-1 virus without causing excessive damage to said primary peripheral blood mononuclear cells.

2. The method for inhibiting HIV-1 in a human or animal in need thereof of claim 1, wherein said disaccharide arabinogalactan contains one or more analogs chosen from the group consisting of Galactose Analogs, Lactose Analogs, α-D-Arabinopvranose Analogs, 2-Deoxyglucose Analogs, Galactose-Arabinopyranose Analogs and cycloartane isolates.

3. The method for inhibiting HIV-1 in a human or animal in need thereof of claim 1, further comprising a step of isolating said disaccharide arabinogalactan after said extracting step.

4. The method for inhibiting HIV-1 in a human or animal in need thereof of claim 1, wherein said disaccharide arabinogalactan comprises an analog having one of the following chemical structures:

or

-continued

5. A method for inhibiting HIV-1 in a human or animal in need thereof comprising:
   obtaining a quantity of indigenous Jamaican plant *GuaiacumOfficinale* L.;
   extracting indigenous Jamaican plant *Guaiacum Officinale* L. with methanol to produce a crude extract;
   fractionating said crude extract; to produce a disaccharide arabinogalactan fraction
   administering a therapeutically effective amount of the disaccharide arabinogalactan fraction of said crude extract in the bloodstream of said human or animal in need thereof to expose the primary peripheral blood mononuclear cells of the human or animal thereto;
   said therapeutically effective amount of said disaccharide arabinogalactan fraction eliciting an inhibitory response of HIV-1 virus without causing excessive damage to said primary peripheral blood mononuclear cells.

6. The method for inhibiting HIV-1 in a human or animal in need thereof of claim 5, further comprising a step of diluting said disaccharide arabinogalactan into a pharmaceutically-acceptable concentration.

7. The method for inhibiting HIV-1 in a human or animal in need thereof of claim 5, wherein said disaccharide arabinogalactan fraction contains one or more analogs chosen from the group consisting of Galactose Analogs, Lactose Analogs, α-D-Arabinopyranose Analogs, 2-Deoxyglucose Analogs, Galactose-Arabinopyranose Analogs, and cycloartane isolates.

8. The method for inhibiting HIV-1 in human or animal in need thereof of claim 5, further comprising a step of isolating said disaccharide arabinogalactan fraction.

9. The method for inhibiting HIV-1 human or animal in need thereof of claim 5, wherein said disaccharide arabinogalactan fraction comprises an analog having one of the following chemical structures:

* * * * *